United States Patent
Blumenkranz et al.

(10) Patent No.: US 8,621,939 B2
(45) Date of Patent: *Jan. 7, 2014

(54) RIBBED FORCE SENSOR

(71) Applicant: Intuitive Surgical Operations, Inc., Sunnyvale, CA (US)

(72) Inventors: Stephen J. Blumenkranz, Los Altos Hills, CA (US); Christopher J. Hasser, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/932,128

(22) Filed: Jul. 1, 2013

(65) Prior Publication Data

US 2013/0291654 A1 Nov. 7, 2013

Related U.S. Application Data

(63) Continuation of application No. 11/958,772, filed on Dec. 18, 2007, now Pat. No. 8,496,647.

(51) Int. Cl.
*G01D 7/00* (2006.01)
*A61B 19/00* (2006.01)

(52) U.S. Cl.
USPC ............ 73/862.046; 73/862.041; 73/862.042; 73/862.043; 73/862.044; 73/862.045; 606/1; 606/130

(58) Field of Classification Search
USPC .............. 73/744, 800, 862.41–862.46; 606/1, 606/130
See application file for complete search history.

(56) References Cited

U.S. PATENT DOCUMENTS

| | | | | |
|---|---|---|---|---|
| 3,985,025 A | * | 10/1976 | Ormond | 177/255 |
| 4,094,192 A | * | 6/1978 | Watson et al. | 73/862.044 |
| 4,448,083 A | * | 5/1984 | Hayashi | 73/862.042 |
| 4,577,513 A | * | 3/1986 | Harwood et al. | 73/862.045 |
| 4,580,551 A | | 4/1986 | Siegmund et al. | |
| 4,640,138 A | * | 2/1987 | Meyer et al. | 73/862.045 |
| 4,762,006 A | * | 8/1988 | Asakawa et al. | 73/862.044 |
| 4,763,531 A | * | 8/1988 | Dietrich et al. | 73/862.044 |
| 5,450,746 A | | 9/1995 | Howard | |

(Continued)

FOREIGN PATENT DOCUMENTS

| | | |
|---|---|---|
| DE | 10013059 A1 | 9/2001 |
| DE | 202007010974 U1 | 10/2007 |

(Continued)

OTHER PUBLICATIONS

FR2435329A1, Translation. Inventors: Lande Maurice et al. Title: A Manipulator, Particularly an Automatic Paint, Capable of Learning Date: Apr. 4, 1980.

(Continued)

*Primary Examiner* — Sam Yao
*Assistant Examiner* — Boniface N Nganga

(57) ABSTRACT

In one embodiment, a force sensor apparatus is provided including a tube portion having a plurality of radial ribs and a strain gauge positioned over each of the plurality of radial ribs, a proximal end of the tube portion that operably couples to a shaft of a surgical instrument that operably couples to a manipulator arm of a robotic surgical system, and a distal end of the tube portion that proximally couples to a wrist joint coupled to an end effector.

20 Claims, 17 Drawing Sheets

(56) References Cited

U.S. PATENT DOCUMENTS

| | | | |
|---|---|---|---|
| 5,513,536 A | | 5/1996 | Reger et al. |
| 5,631,973 A | | 5/1997 | Green |
| 5,767,840 A | * | 6/1998 | Selker .......................... 345/161 |
| 5,807,377 A | | 9/1998 | Madhani et al. |
| 5,889,214 A | * | 3/1999 | Kang et al. ............... 73/862.044 |
| 5,894,094 A | * | 4/1999 | Kuchler et al. ........... 73/862.044 |
| 5,969,268 A | * | 10/1999 | Sommerfeld et al. ... 73/862.041 |
| 6,038,933 A | * | 3/2000 | Meyer ....................... 73/862.045 |
| 6,322,090 B1 | | 11/2001 | Chignoli et al. |
| 6,331,181 B1 | | 12/2001 | Tierney et al. |
| 6,332,090 B1 | | 12/2001 | DeFrank et al. |
| 6,349,604 B1 | * | 2/2002 | Byun et al. ............... 73/862.043 |
| 6,371,952 B1 | | 4/2002 | Madhani et al. |
| 6,470,205 B2 | | 10/2002 | Bosselmann et al. |
| 6,477,904 B2 | * | 11/2002 | Maeda et al. ............ 73/862.044 |
| 6,491,701 B2 | | 12/2002 | Tierney et al. |
| 6,532,830 B1 | * | 3/2003 | Jansen et al. ............. 73/862.042 |
| 6,574,355 B2 | | 6/2003 | Green |
| 6,587,750 B2 | | 7/2003 | Gerbi et al. |
| 6,622,575 B1 | * | 9/2003 | Nagata ..................... 73/862.042 |
| 6,666,079 B2 | * | 12/2003 | Poulbot et al. .................. 73/146 |
| 6,676,684 B1 | | 1/2004 | Morley et al. |
| 6,770,081 B1 | | 8/2004 | Cooper et al. |
| 6,783,524 B2 | | 8/2004 | Anderson et al. |
| 6,817,974 B2 | | 11/2004 | Cooper et al. |
| 6,835,173 B2 | | 12/2004 | Couvillon, Jr. |
| 6,866,671 B2 | | 3/2005 | Tierney et al. |
| 6,871,552 B2 | * | 3/2005 | Liu et al. .................. 73/862.041 |
| 6,879,880 B2 | | 4/2005 | Nowlin et al. |
| 6,902,560 B1 | | 6/2005 | Morley et al. |
| 6,936,042 B2 | | 8/2005 | Wallace et al. |
| 7,174,792 B2 | * | 2/2007 | Ealey ........................ 73/862.041 |
| 7,437,954 B2 | * | 10/2008 | Sakano ..................... 73/862.044 |
| 7,441,470 B2 | * | 10/2008 | Morimoto ................ 73/862.045 |
| 7,500,406 B2 | * | 3/2009 | Morimoto ................ 73/862.044 |
| RE40,891 E | * | 9/2009 | Yasutake ....................... 345/173 |
| 7,594,445 B2 | * | 9/2009 | Hirabayashi et al. .... 73/862.044 |
| 7,603,917 B2 | * | 10/2009 | Graham et al. .......... 73/862.043 |
| 7,646,945 B2 | * | 1/2010 | Jones et al. ....................... 385/13 |
| 7,665,371 B2 | * | 2/2010 | Mastinu et al. .......... 73/862.041 |
| 7,779,705 B2 | * | 8/2010 | Mastinu et al. ............. 73/862.381 |
| 2004/0035216 A1 | * | 2/2004 | Morrison et al. ................ 73/800 |
| 2004/0045372 A1 | * | 3/2004 | Liu et al. .................. 73/862.041 |
| 2005/0200324 A1 | | 9/2005 | Guthart et al. |
| 2006/0027031 A1 | * | 2/2006 | Ealey ........................ 73/862.041 |
| 2006/0161138 A1 | | 7/2006 | Orban, III |
| 2006/0213287 A1 | * | 9/2006 | Sakano ..................... 73/862.042 |
| 2007/0107536 A1 | * | 5/2007 | Mastinu et al. .......... 73/862.043 |
| 2007/0137371 A1 | | 6/2007 | Devengenzo et al. |
| 2007/0151390 A1 | | 7/2007 | Blumenkranz et al. |
| 2007/0151391 A1 | | 7/2007 | Larkin et al. |
| 2008/0211293 A1 | * | 9/2008 | Ai et al. ..................... 301/105.1 |
| 2008/0226409 A1 | | 9/2008 | Hasenzahl |
| 2009/0157092 A1 | | 6/2009 | Blumenkranz et al. |

FOREIGN PATENT DOCUMENTS

| | | |
|---|---|---|
| FR | 2435329 A1 | 4/1980 |
| FR | 2693397 A1 | 1/1994 |
| WO | 2007120329 A2 | 10/2007 |
| WO | 2007120329 A3 | 10/2007 |

OTHER PUBLICATIONS

FR2693397A1, Translation. Inventors: Jean-Marc et al. Title: Master-slave Remote Handling Device—in Radioactive Hot Cell with Resistance Strain Gauges Monitoring Force Applied to Handle to Actuate Alarm if Force is Excessive Date: Jan. 4, 1994.

Berkelman P.J., et al., "A Miniature Instrument Tip Force Sensor for Enhanced Force Feedback During Robot-Assisted Manipulation," IEEE Transaction on Robotics and Automation, Oct. 5, 2003, vol. 19 (5), pp. 917-922.

Cepolina F. et al., "Review of robotic fixtures for minimally invasive surgery," International Journal of Medical Robotics and Computer Assisted Surgery, 2004, pp. 43-63, vol. 1, Issue-1.

EP08861934.1 Communication pursuant to Article 94(3) EPC, dated Nov. 11, 2010, 6 pages.

PCT/US08/86240 International Search Report and Written Opinion of the International Search Authority, mailed Mar. 13, 2009, 12 pages.

Peirs, Jan et al., "A micro optical force sensor for force feedback during minimally invasive robotic surgery," Sensors and Actuators A, 2004, pp. 447-455, vol. 115.

Seibold U., et al., "Prototype of Instrument for Minimally Invasive Surgery with 6-Axis Force Sensing Capability," Proceedings of the 2005 IEEE International Conference on Robotics and Automation Barcelona, Spain, Apr. 2005, pp. 498-503.

U.S. Appl. No. 60/755,108, filed on Dec. 30, 2005, Blumenkranz, Stephen J. et al.

U.S. Appl. No. 60/755,157, filed Dec. 30, 2005, Larkin, David Q.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

FIG. 5C1

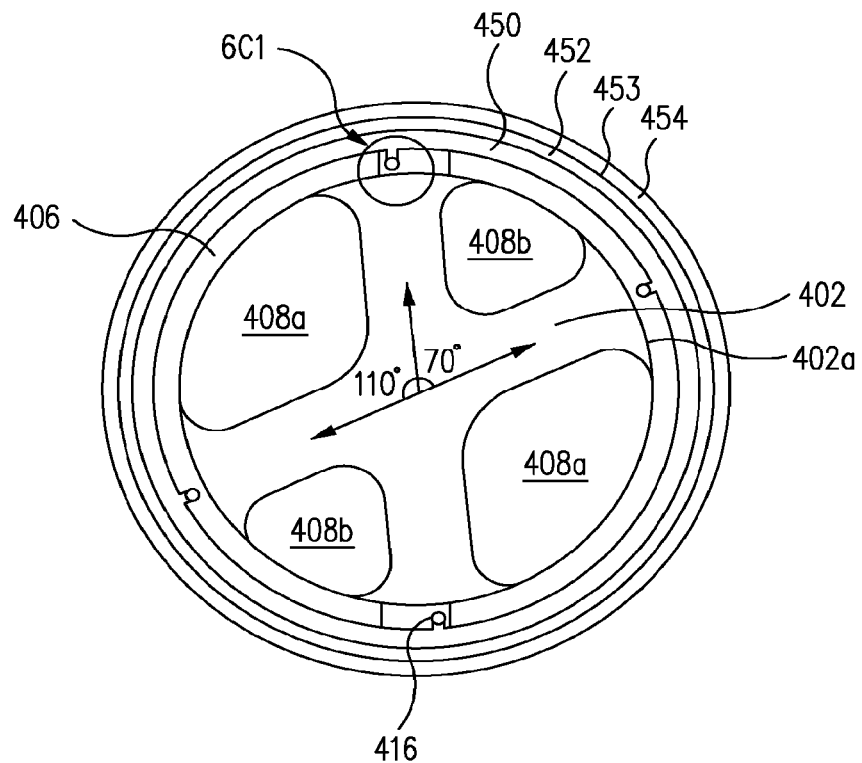
FIG. 6C
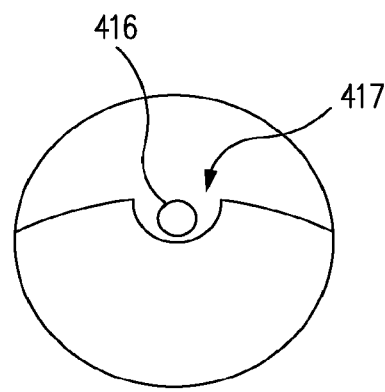
FIG. 6C1

FIG. 7B1

RIBBED FORCE SENSOR

CROSS-REFERENCE TO RELATED APPLICATIONS AND PATENTS

This application is a continuation of U.S. patent application Ser. No. 11/958,772 (filed Dec. 18, 2007), which is incorporated by reference herein in its entirety for all purposes.

This application is related to U.S. Provisional Application No. 60/755,108 filed Dec. 30, 2005, U.S. Provisional Application 60/755,157 filed Dec. 30, 2005, U.S. application Ser. No. 11/553,303 filed Oct. 26, 2006, U.S. patent application Ser. No. 11/537,241 filed Sep. 29, 2006, U.S. patent application Ser. No. 11/093,372 filed Mar. 30, 2005, and U.S. Pat. Nos. 6,936,042, 6,902,560, 6,879,880, 6,866,671, 6,817,974, 6,783,524, 6,676,684, 6,371,952, 6,331,181, and 5,807,377, the full disclosures of which are incorporated by reference herein for all purposes.

TECHNICAL FIELD

The present invention relates generally to surgical robot systems and, more particularly, to an improved system, apparatus, and method for sensing forces applied to a surgical instrument.

BACKGROUND

In robotically-assisted surgery, the surgeon typically operates a master controller to control the motion of surgical instruments at the surgical site from a location that may be remote from the patient (e.g., across the operating room, in a different room or a completely different building from the patient). The master controller usually includes one or more hand input devices, such as handheld wrist gimbals, joysticks, exoskeletal gloves, handpieces, or the like, which are operatively coupled to the surgical instruments through a controller with servo motors for articulating the instruments' position and orientation at the surgical site. The servo motors are typically part of an electromechanical device or surgical manipulator arm ("the slave") that includes a plurality of joints, linkages, etc., that are connected together to support and control the surgical instruments that have been introduced directly into an open surgical site or through trocar sleeves (cannulas) inserted through incisions into a body cavity, such as the patient's abdomen. There are available a variety of surgical instruments, such as tissue graspers, needle drivers, electrosurgical cautery probes, etc., to perform various functions for the surgeon, e.g., retracting tissue, holding or driving a needle, suturing, grasping a blood vessel, dissecting, cauterizing, coagulating tissue, etc. A surgeon may employ a large number of different surgical instruments/tools during a procedure.

This new surgical method through remote manipulation has created many new challenges. One such challenge is providing the surgeon with the ability to accurately "feel" the tissue that is being manipulated by the surgical instrument via the robotic manipulator. The surgeon must rely on visual indications of the forces applied by the instruments or sutures. It is desirable to sense the forces and torques applied to the tip of the instrument, such as an end effector (e.g., jaws, grasper, blades, etc.) of robotic minimally invasive surgical instruments, in order to feed the forces and torques back to the surgeon user through the system hand controls or by other means, such as visual display, vibrations, or audible tone. One device for this purpose from the laboratory of G. Hirzinger at DLR Institute of Robotics and Mechatronics is described in "Review of Fixtures for Low-Invasiveness Surgery" by F. Cepolina and R. C. Michelini, *Int'l Journal of Medical Robotics and Computer Assisted Surgery*, Vol. 1, Issue 1, page 58, the contents of which are incorporated by reference herein for all purposes. However, that design disadvantageously places a force sensor distal to (or outboard of) the wrist joints, thus requiring wires or optic fibers to be routed through the flexing wrist joint and also requiring the yaw and grip axes to be on separate pivot axes.

Another problem has been fitting and positioning the necessary wires, rods, or tubes for mechanical actuation of end effectors in as small a space as possible because relatively small instruments are typically desirable for performing surgery.

What is needed, therefore, are improved telerobotic systems and methods for remotely controlling surgical instruments at a surgical site on a patient. In particular, these systems and methods should be configured to provide accurate feedback of forces and torques to the surgeon to improve user awareness and control of the instruments.

SUMMARY

The present invention provides an apparatus, system, and method for improving force and torque feedback to and sensing by a surgeon performing a robotic surgery. In one embodiment, a force sensor includes a tube portion that includes a plurality of radial ribs and a strain gauge positioned over each of the plurality of radial ribs. A proximal part of the tube portion is coupled to a shaft of a surgical instrument that may be operably coupled to a manipulator arm of a robotic surgical system. A distal part of the tube portion is coupled to a wrist joint coupled to an end effector. The couplings may be direct or indirect with an intermediate mechanical component between the coupled parts.

Groups of strain gauges are positioned on or near a distal end of an instrument shaft proximal to (i.e., inboard of) a moveable wrist of a robotic surgical instrument via an apparatus that senses forces and torques at the distal tip of the instrument without errors due to changes in the configuration of the tip (such as with a moveable wrist) or steady state temperature variations.

Advantageously, the present invention improves the sensing and feedback of forces and/or torques to the surgeon and substantially eliminates the problem of passing delicate wires, or optic fibers through the flexible wrist joint of the instrument. A force sensor apparatus may be manufactured, tested, and calibrated as a separate modular component and brought together with other components in the conventional instrument assembly process. The force sensor apparatus may also be manufactured as an integrated part of the instrument. In addition, it is possible to choose a material for the sensor structural member different from the material of the instrument shaft whose design considerations may compromise the mechanical properties required for the sensor.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 5C1 illustrates a magnified section labeled 5C1 in FIG. 5C.

FIG. 6C illustrates an end view of the force sensor apparatus of FIGS. 6A and 6B including radial ribs positioned in non-uniform angles, and FIG. 6C1 illustrates a magnified section labeled 6C1 in FIG. 6C, in accordance with another embodiment of the present invention.

FIG. 7B1 illustrates a magnified section labeled 7B1 in FIG. 7B, in accordance with another embodiment of the present invention.

Figure 1A:
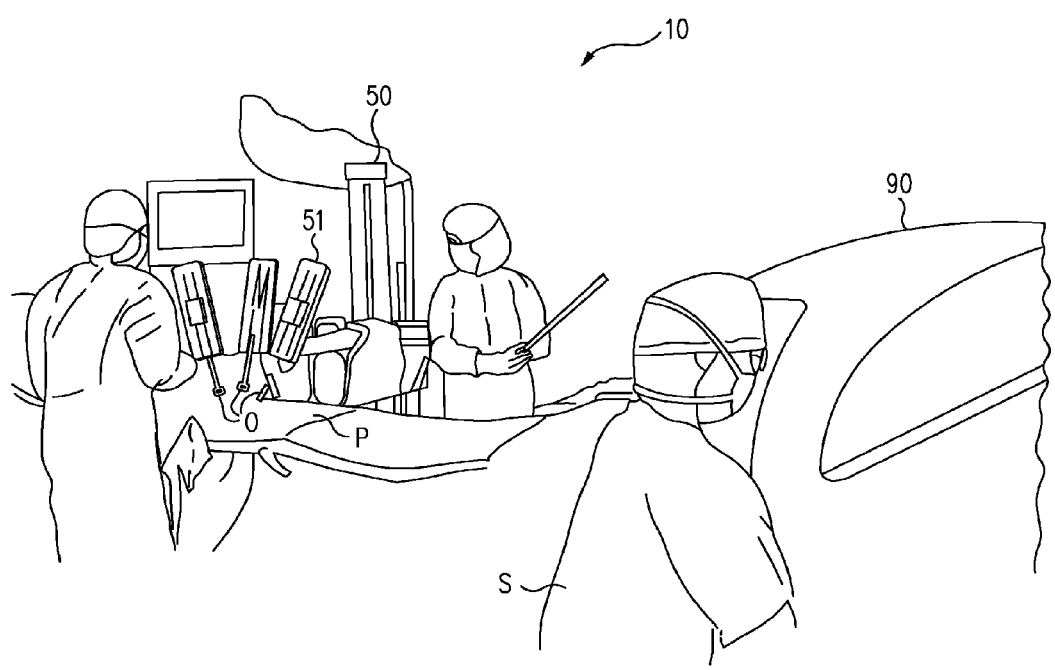
FIG. 1A is a perspective view of a robotic surgical system in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system, apparatus, and method for sensing forces applied to tissue while performing robotically-assisted surgical procedures on a patient, particularly including open surgical procedures, neurosurgical procedures, and minimally invasive procedures, such as laparoscopy, arthroscopy, thoracoscopy, and the like. The apparatus and method of the present invention are particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master having six or more degrees of freedom (e.g., 3 degrees of freedom for position and 3 degrees of freedom for orientation) to form a telepresence system with force reflection or other scalar force magnitude display. A description of a suitable slave-master system can be found in U.S. Pat. No. 6,574,355, the complete disclosure of which is incorporated herein by reference for all purposes.

Figure 1B:
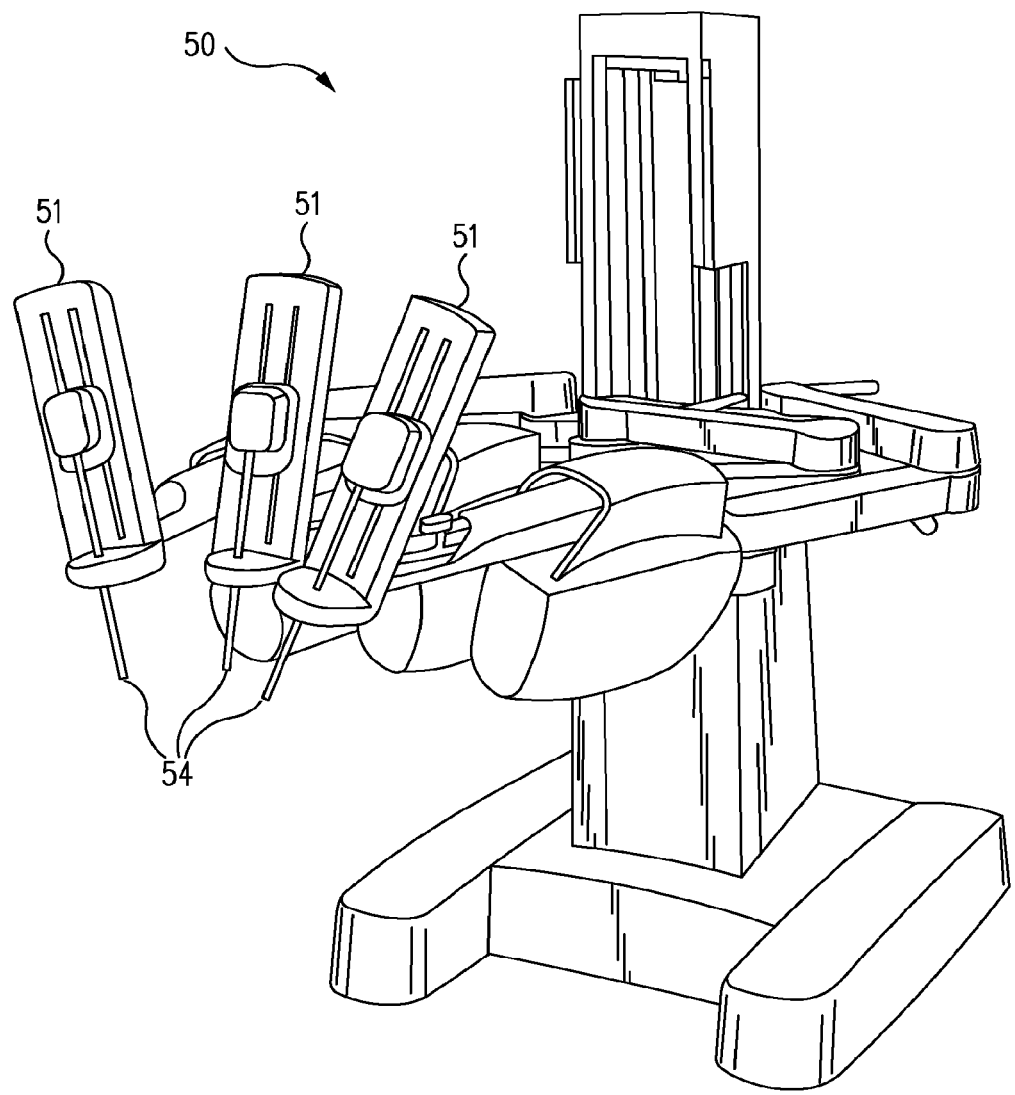
FIG. 1B is a perspective view of a robotic surgical arm cart system of the robotic surgical system in FIG. 1A in accordance with an embodiment of the present invention.
Figure 1C:
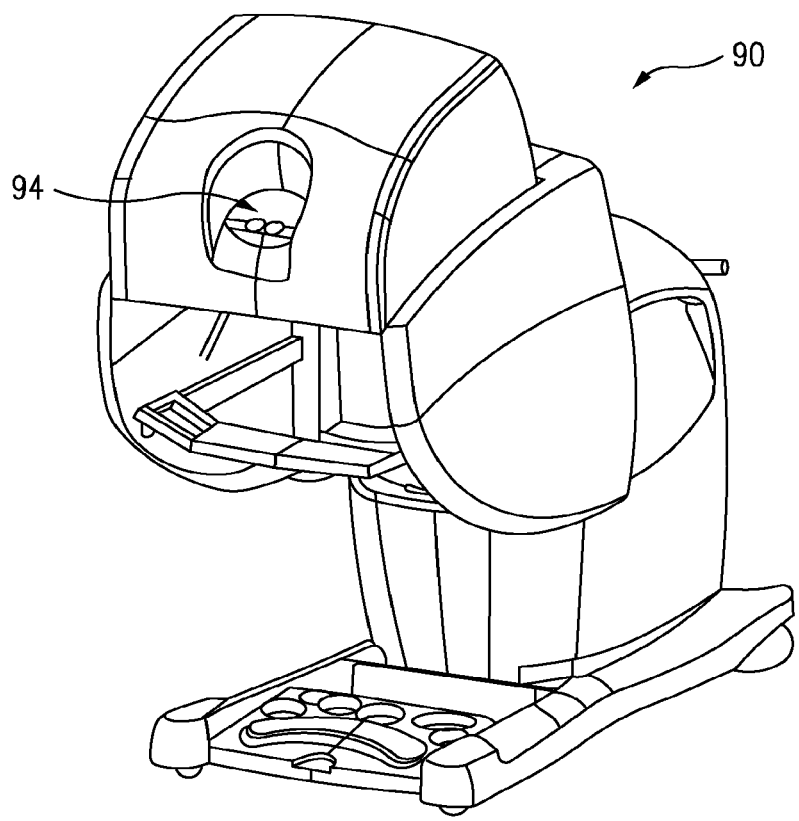
FIG. 1C is a front perspective view of a master console of the robotic surgical system in FIG. 1A in accordance with an embodiment of the present invention.

Referring to the drawings in detail, wherein like numerals indicate like elements, a robotic surgical system 10 is illustrated according to an embodiment of the present invention. As shown in FIGS. 1A through 1C, robotic system 10 generally includes one or more surgical manipulator assemblies 51 mounted to or near an operating table O and a master control assembly located at a surgeon's console 90 for allowing the surgeon S to view the surgical site and to control the manipulator assemblies 51. The system 10 will also include one or more viewing scope assemblies and a plurality of surgical instrument assemblies 54 adapted for being removably coupled to the manipulator assemblies 51 (discussed in more detail below). Robotic system 10 includes at least two manipulator assemblies 51 and preferably at least three manipulator assemblies 51. The exact number of manipulator assemblies 51 will depend on the surgical procedure and the space constraints within the operating room among other factors. As discussed in detail below, one of the assemblies 51 will typically operate a viewing scope assembly (e.g., in endoscopic procedures) for viewing the surgical site, while the other manipulator assemblies 51 operate surgical instruments 54 for performing various procedures on the patient P.

The control assembly may be located at a surgeon's console 90 which is usually located in the same room as operating table O so that the surgeon may speak to his/her assistant(s) and directly monitor the operating procedure. However, it should be understood that the surgeon S can be located in a different room or a completely different building from the patient P. The master control assembly generally includes a support, a monitor for displaying an image of the surgical site to the surgeon S, and one or more master(s) for controlling manipulator assemblies 51. Master(s) may include a variety of input devices, such as hand-held wrist gimbals, joysticks, gloves, trigger-guns, hand-operated controllers, voice recognition devices, or the like. Preferably, master(s) will be provided with the same degrees of freedom as the associated surgical instrument assemblies 54 to provide the surgeon with telepresence, the perception that the surgeon is immediately adjacent to and immersed in the surgical site, and intuitiveness, the perception that the master(s) are integral with the instruments 54 so that the surgeon has a strong sense of directly and intuitively controlling instruments 54 as if they are part of or held in his/her hands. Position, force, and tactile feedback sensors (not shown) may also be employed on instrument assemblies 54 to transmit position, force, and tactile sensations from the surgical instrument back to the surgeon's hands, ears, or eyes as he/she operates the telerobotic system. One suitable system and method for providing telepresence to the operator is described in U.S. Pat. No. 6,574,355, which has previously been incorporated herein by reference.

The monitor 94 will be suitably coupled to the viewing scope assembly such that an image of the surgical site is provided adjacent the surgeon's hands on surgeon console. Preferably, monitor 94 will display an image on a display that is oriented so that the surgeon feels that he or she is actually looking directly down onto the operating site. To that end, an image of the surgical instruments 54 appears to be located substantially where the operator's hands are located even though the observation points (i.e., the endoscope or viewing camera) may not be from the point of view of the image. In addition, the real-time image is preferably transformed into a stereo image such that the operator can manipulate the end effector and the hand control as if viewing the workspace in substantially true presence. By true presence, it is meant that the presentation of an image is a true stereo image simulating the viewpoint of an operator that is physically manipulating the surgical instruments 54. Thus, a controller (not shown) transforms the coordinates of the surgical instruments 54 to a perceived position so that the stereo image is the image that one would see if the camera or endoscope were located directly behind the surgical instruments 54. A suitable coordinate transformation system for providing this virtual image is described in U.S. Pat. No. 5,631,973, the complete disclosure of which is incorporated herein by reference for all purposes.

A servo control is provided for transferring the mechanical motion of masters to manipulator assemblies 51. The servo control may be separate from, or integral with, manipulator assemblies 51. The servo control will usually provide force and torque feedback from the surgical instruments 54 to the hand-operated masters. In addition, the servo control may include a safety monitoring controller (not shown) to safely halt system operation, or at least inhibit all robot motion, in response to recognized undesirable conditions (e.g., exertion of excessive force on the patient, mismatched encoder readings, etc.). The servo control preferably has a servo bandwidth with a 3 dB cut off frequency of at least 10 Hz so that the system can quickly and accurately respond to the rapid hand motions used by the surgeon and yet to filter out undesirable surgeon hand tremors. To operate effectively with this system, manipulator assemblies 51 have a relatively low inertia, and the drive motors have relatively low ratio gear or pulley couplings. Any suitable conventional or specialized servo control may be used in the practice of the present invention, with those incorporating force and torque feedback being particularly preferred for telepresence operation of the system.

Figure 2:
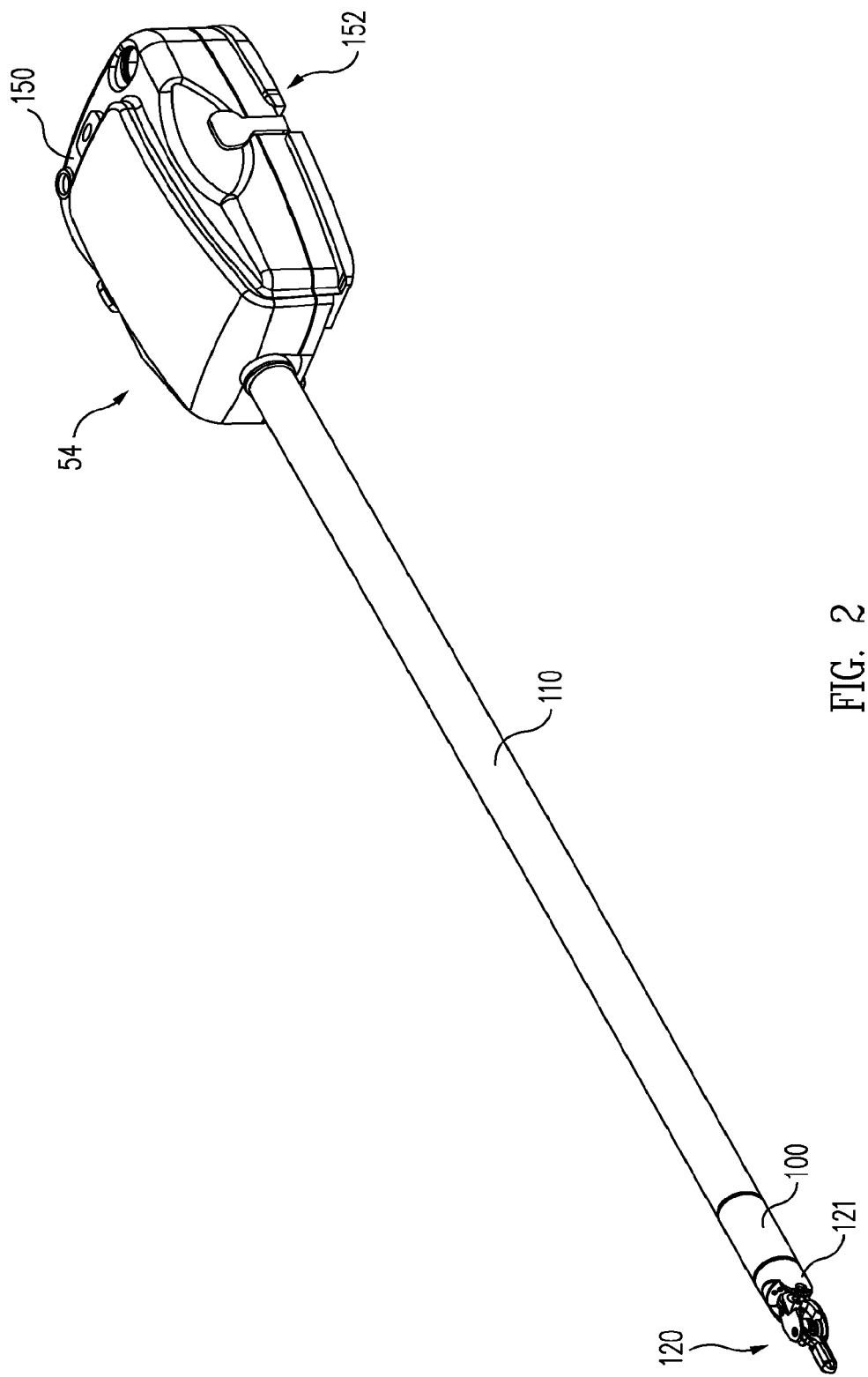
FIG. 2 is a perspective view of a surgical instrument including a force sensor apparatus operably coupled proximal (or inboard) to a wrist joint in accordance with an embodiment of the present invention.

Referring to FIG. 2, a perspective view is shown of a surgical instrument 54 including a force sensor apparatus 100 operably coupled to a distal end of a rigid shaft 110 and proximal to a wrist joint 121 in accordance with an embodiment of the present invention. An end portion 120, such as a surgical end effector, is coupled to force sensor apparatus 100 via the wrist joint 121. A housing 150 is operably coupled to a proximal end of the rigid shaft 110 and includes an interface 152 which mechanically and electrically couples instrument 54 to the manipulator 51.

Figure 3A:
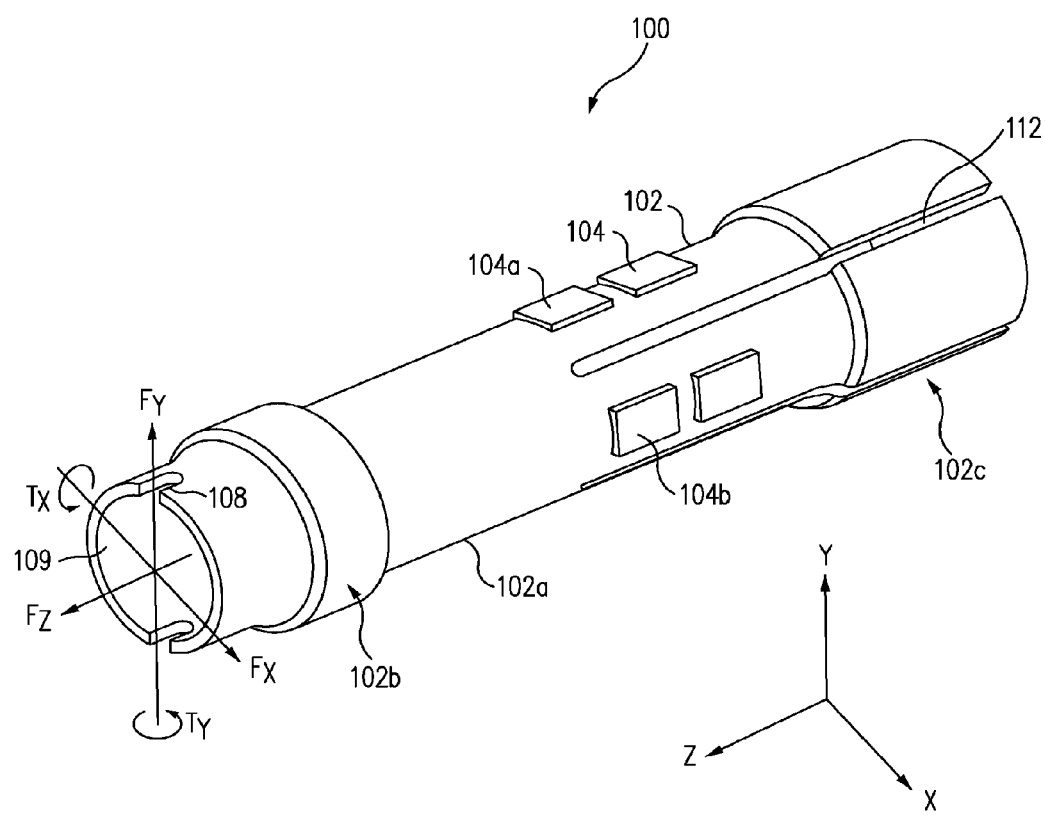
FIG. 3A is a perspective view of a force sensor apparatus in accordance with an embodiment of the present invention.
Figure 3B:
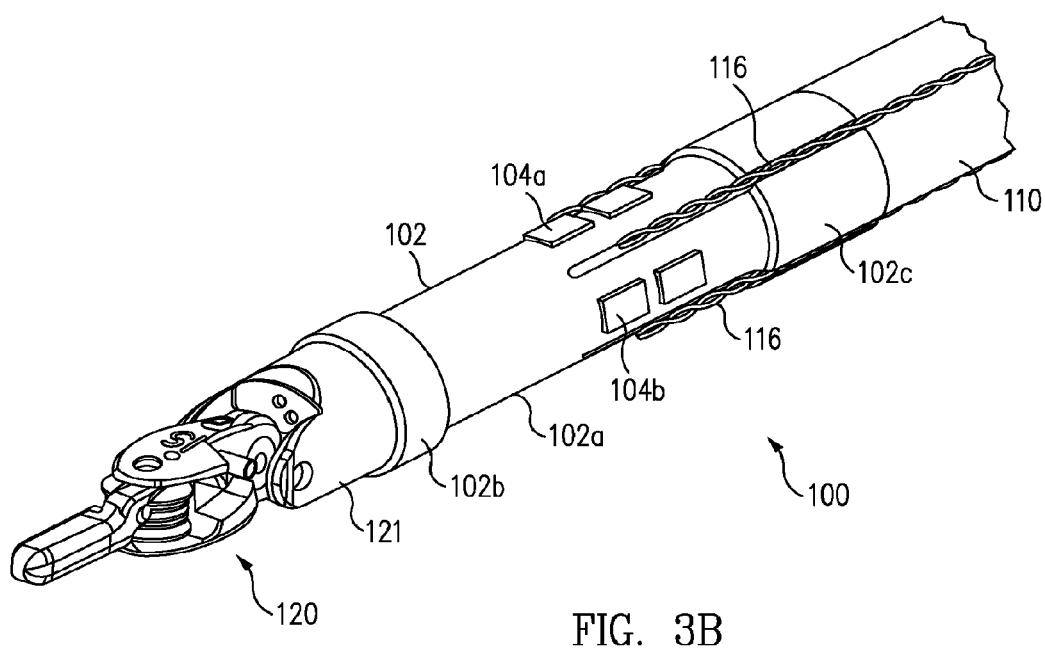
FIG. 3B illustrates the force sensor of FIG. 3A operably coupled to a shaft and end portion of a surgical instrument in accordance with an embodiment of the present invention.
Figure 3C:
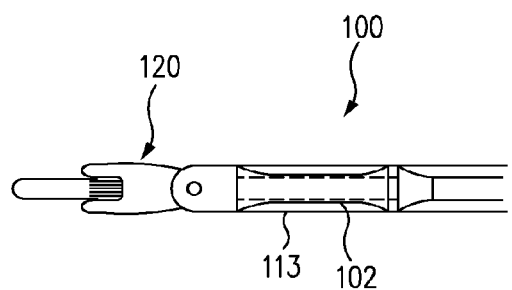
FIG. 3C illustrates the force sensor of FIG. 3A with a protective cover over a portion of the force sensor in accordance with an embodiment of the present invention.

Referring now to FIGS. 3A-3C in conjunction with FIGS. 1A-1C and 2, an improved apparatus, system, and method for sensing and feedback of forces and/or torques to the surgeon will be described in accordance with an embodiment of the present invention. FIG. 3A shows a perspective view of force sensor apparatus 100 including in one embodiment a tube 102 including a number (e.g., 3, 4, 6, or 8) of strain gauges 104 (e.g., 104a and 104b) mounted to a surface of tube 102 and oriented axially (parallel to the lengthwise axis z of the tube). FIG. 3B shows the force sensor apparatus 100 of FIG. 3A operably coupled to a shaft 110 and end portion 120 of a surgical instrument in accordance with an embodiment of the present invention. FIG. 3C shows a cross-section view of force sensor apparatus 100 including a cover or sleeve 113 over tube 102.

In accordance with an embodiment of the present invention, force sensor apparatus 100 is a separately manufacturable module or part adapted for incorporation as part of the shaft 110 of surgical instrument 54 at a prescribed distance from the tip where there may be an articulated wrist with specialized jaws, cutting devices, or other end portion 120. In one example, tube 102 may be made of a sufficiently strong material and may be spool shaped, including end portions 102b, 102c with a depressed portion 102a therebetween that is smaller in diameter than end portions 102b, 102c. Strain gauges 104 may be mounted on the surface of depressed portion 102a. Proximal tube portion 102c operably couples to the shaft 110 of surgical instrument 54 and distal tube portion 102b operably couples to a wrist joint 121. In one example, the diameter of the completed force sensor apparatus matches the diameter of the instrument shaft, thus allowing the entire assembly of the instrument (including the coupled force sensor apparatus) to pass through a cannula or a seal without added friction or snagging.

Force sensor apparatus 100 includes a through passage 109 for end portion actuation cables or rods. End features 108 of end portion 102b insure secure mounting and angular alignment to the main instrument shaft and wrist/jaw/other end portion sub-assembly of the instrument. Wire leads or optic fibers 116 (e.g., shielded twisted pairs, coax, or fiber) from the strain gauges 104 may be inlaid into grooves 112 in proximal tube portion 102c of tube 102 and matching grooves in the shaft 110 of the surgical instrument 54. The wire leads or optic fibers 116 may then be embedded in an adhesive bonding or potting compound such as epoxy.

In one embodiment, as illustrated in FIG. 3C, cover 113 is positioned over and encapsulates the mounted strain gauges 104 and other circuit elements on the surface of the tube 102, thereby providing mechanical protection of the sensors. In one example, cover 113 is a mechanically protective woven sleeve potted on depressed portion 102a and is comprised of a woven resin impregnated fiberglass or metal braid electrical shielding.

As disclosed in U.S. patent application Ser. No. 11/537,241, filed Sep. 29, 2006, the contents of which have been previously incorporated by reference, strain gauges 104 may be spaced in a ring at intervals around the circumference of the tube 102 (e.g., 3 gauges at 120 degrees, 4 gauges at 90 degrees, or 4 gauges at 70 degrees and 110 degrees). The signals from the sensors are combined arithmetically in various sums and differences to obtain measures of three perpendicular forces (e.g., $F_x$, $F_y$, and $F_z$) exerted upon the instrument tip and the torques about the two axes perpendicular to the shaft axis (i.e., axes x and y). In accordance with the present invention, the measurement of the forces is made independent of the orientation and effective lever arm length of an articulated wrist mechanism at the distal end of the instrument when two axially separated sets or rings of gauges are utilized. Forces exerted against end portion 120 are detected by the force sensing elements via an interrogator, which may be operably coupled to the servo control or to a processor for notifying the surgeon of these forces (e.g., via master(s) or a display). It is understood that by adding a second ring of similarly oriented gauges (e.g., two sets of 3 gauges or two sets of 4 gauges) at a different axial position on the tube, additional applied torque information (e.g., $T_x$ and $T_y$) may be obtained, and dependence of the force data on instrument wrist length, orientation, and resulting jaw distance may be eliminated.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft.

Both fiber technologies require an interrogator unit that decodes the optically encoded strain information into electrical signals compatible with the computer control hardware or display means of the robotic surgical system. A processor may then be used to calculate forces according to the signals from the strain gauges/sensors.

Additionally, there may be co-mounted unstrained gauges or Poisson strained gauges oriented in the circumferential direction adjacent to each axial gauge and incorporated in the bridge completion circuits to eliminate temperature effects. The strain gauge bridge circuits are completed in a manner to give the best signal for bending loads due to the lateral forces ($F_x$ and $F_y$) exerted on the instrument tip jaws.

For resistive foil or semiconductor strain gauges, active components such as bare die op-amps and passive components such as secondary resistors or capacitors may be attached adjacent to the strain gauges connected by bond wires or thick film circuit traces in the manner of hybrid circuits to amplify, filter, and/or modulate the gauge output signals to reject noise sources. Such components are not needed for fiber optic gauges.

Surgical instrument 54 to which force sensor apparatus 100 couples may include a circumferentially coiled insulated flex circuit style service loop of parallel conductive traces at the proximal end of the instrument shaft 110 permitting the substantially free rotation of the instrument shaft while conducting the input gauge excitation power and output gauge signals to stationary housing 150 of the instrument 54.

Housing 150 operably interfaces with a robotic manipulator arm 51, in one embodiment via a sterile adaptor interface 152. Applicable housings, sterile adaptor interfaces, and manipulator arms are disclosed in U.S. patent application Ser. No. 11/314,040 filed on Dec. 20, 2005, and U.S. application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 120 has a range of motion that includes pitch and yaw motion about the x- and y-axes and rotation about the z-axis (as shown in FIG. 3A). These motions as well as actuation of an end effector are provided via cables and/or rods running through shaft 110 and into housing 150 that transfer motion from the manipulator arm 51. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, irrigators, catheters, and suction orifices. Alternatively, the surgical instrument may comprise an electrosurgical probe for ablating, resecting, cutting or coagulating tissue. Such surgical instruments are available from Intuitive Surgical, Inc. of Sunnyvale, Calif.

For the methods and apparatus mentioned above, it may be advantageous to use a calibration process in which combinations of forces and torques are applied to the instrument tip serially, simultaneously, or in combinations while correction factors and offsets are determined. The correction factors and offsets may then be applied to the theoretical equations for combining the gauge outputs to obtain $F_x$, $F_y$, $F_z$, $T_x$, and $T_y$. Such a calibration process may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 100 of the present invention is adaptable to the size and shape constraints of various robotic surgical instruments and is suitable for a variety of instruments. Accordingly, end portions 102b, 102c may be formed into various applicable shapes and sizes. Furthermore, force sensor apparatus 100 may be manufactured, tested, and calibrated as a separate modular component and brought together with other components in the conventional instrument assembly process. Also, the sensor may be a slip-on module with suitable electrical contacts that mate with contacts on the instrument shaft permitting a higher value sensor to be used with lower cost instruments of limited cycle life. In addition, the sensor structural member 102 may be comprised of an advantageous material, which may be a different material than the instrument shaft 110 whose design considerations may compromise the properties required for the sensor.

Referring now to FIGS. 4A through 4D, a force sensor apparatus 200 is illustrated in accordance with another embodiment of the present invention. The descriptions of substantially similar parts or elements as those described above with respect to FIGS. 3A-3C are applicable in this embodiment with respect to FIGS. 4A-4D, although redundant descriptions will be omitted.

Figure 4A:
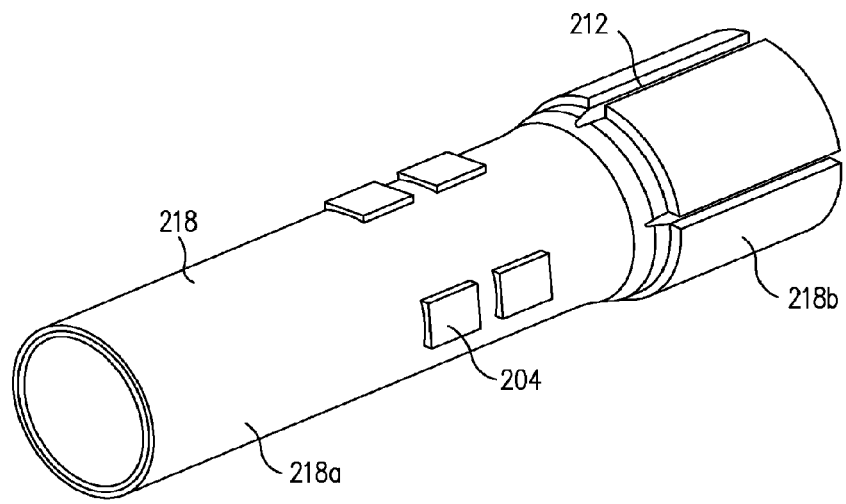
FIG. 4A is a perspective view of an inner tube of a force sensor apparatus in accordance with another embodiment of the present invention.

FIG. 4A is a perspective view of an inner tube 218 of force sensor apparatus 200 in accordance with an embodiment of the present invention. Inner tube 218 includes a proximal raised end portion 218b and a depressed portion 218a smaller in diameter than raised end portion 218b. Strain gauges, as described above with respect to FIGS. 3A-3C, may be mounted on the surface of depressed portion 218a. Raised end portion 218b may include grooves 212 for routing of wire leads or optic fibers from strain gauges 204.

Figure 4B:
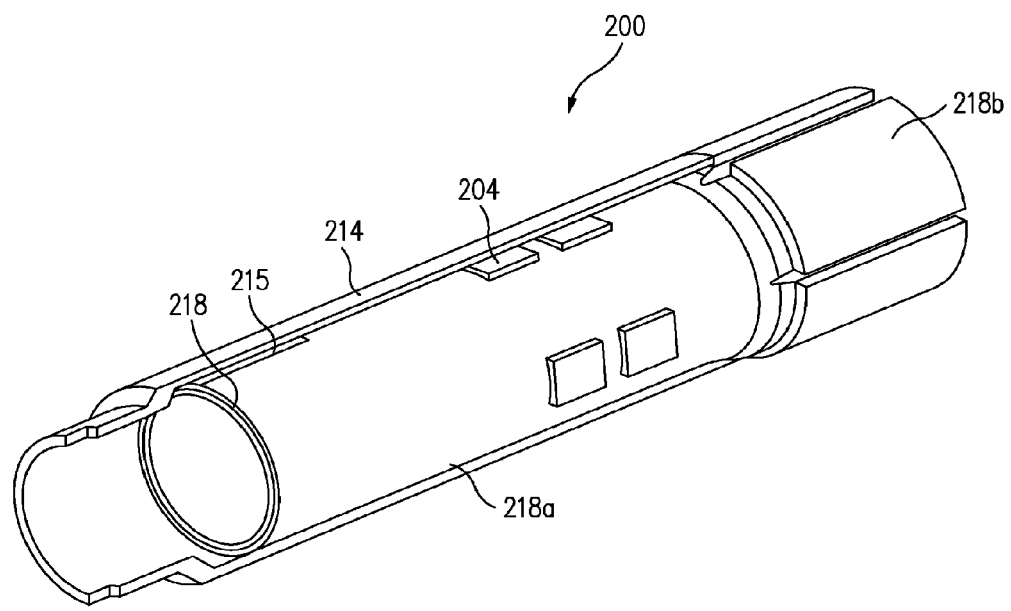
FIG. 4B is a partial cross-sectional view of an outer tube/cover over the inner tube of FIG. 4A of the force sensor apparatus in accordance with an embodiment of the present invention.

FIG. 4B is a partial cross-sectional view of an outer tube 214 over the inner tube 218. In one example, outer tube 214 of force sensor apparatus 200 is a concentric tubular structural member made of sufficiently strong materials that can encapsulate the strain gauges and other electronics within an annular gap between the inner and outer tubes 218 and 214. In one embodiment, the concentric tubes are joined rigidly at the proximal end adjacent proximal portion 218b while a narrow annular gap between the distal ends near a distal portion is filled with an elastomeric material 215 that prevents the high and varying axial forces of the wrist and jaw actuator cable or rods from being transmitted through the inner tube carrying the strain gauges. It is noted that the partially isolated tube carrying the gauges may be either the outer or the inner tube. The non-isolated tube of the pair may carry the entire axial cable load. Preferably, the gauges may be placed on the interior tube to isolate the gauges from the environment. In such an embodiment, the outer tube 214 carries the axial cable forces and also permits the outer tube to provide mechanical protection and potentially act as electromagnetic interference (EMI) shielding to the gauges 204 on the inner tube 218.

Figure 4C:
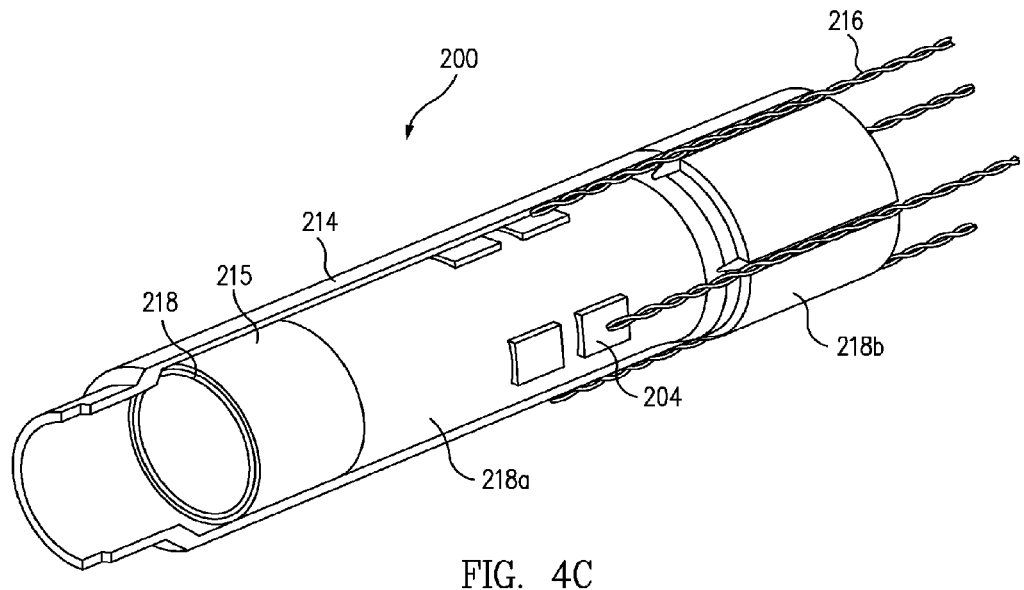
FIG. 4C shows intervening material between the inner and outer tubes of FIG. 4B of the force sensor apparatus and wires or optic fibers operably coupled to the force sensor apparatus in accordance with an embodiment of the present invention.
Figure 4D:
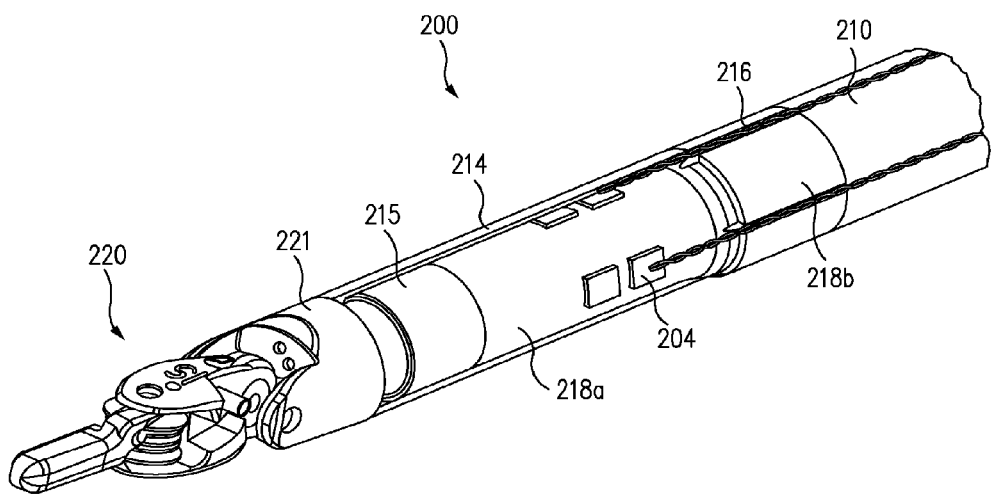
FIG. 4D shows a partial cross-sectional view of the force sensor apparatus operably coupled proximal to (or inboard of) a wrist joint of a surgical instrument in accordance with an embodiment of the present invention.

FIG. 4C highlights elastomeric material 215 between the inner tube 218 and outer tube 214 of the force sensor apparatus 200, and wires or optic fibers 216 operably coupled to gauges 204. FIG. 4D is a partial cross-sectional view of the force sensor apparatus 200 operably coupled proximal to a wrist joint 221 of a surgical instrument in accordance with an embodiment of the present invention. Leads 216 (e.g., shielded twisted pairs, coax, or optic fiber) from the strain gauges 204 may be inlaid into grooves 212 in proximal tube portion 218b of tube 218 and matching grooves in the shaft 210 of a surgical instrument. The leads 216 may then be embedded in an adhesive potting compound such as an epoxy.

In one example, if an outer sensor carrying tube is mounted stationary at the rear mechanism housing, the wire routing may be simplified by not requiring a rotating joint service loop.

Advantageously, the relative shear and compressive properties of elastomers enable this design concept. A suitable elastomer 215 with a low shear modulus permits the relative compression and extension of the cable load carrying tube with respect to the sensor carrying tube (which is connected rigidly at only one end of the tubes as mentioned above). Thus, cable loads and load changes do not affect the sensors. On the other hand, an elastomer confined between two relatively rigid surfaces where the gap between the surfaces is small compared to the extent of the surfaces behaves as a nearly incompressible rigid connection in the direction normal to the confining surfaces, in this case the radial direction of the combined annular tube structure. This causes bending moments carried in the axially loaded tube to be transmitted to and shared by the sensor tube. Thus, the sensor tube can advantageously detect the bending moments due to lateral loads on the instrument wrist and jaws without significant interference or "noise" from the higher varying axial cable loads carried by the other tube. Advantageously, the decoupling of the load carrying members in an endoscopic surgical instrument force sensor enables the separation of undesired jaw actuator tendon forces from desired lateral jaw load induced bending moments on the force sensor.

Alternatively, the desired effect of axially de-constraining the sensor carrying tube from the cable load carrying tube at one end may be obtained by inserting an annular ring of a more rigid low friction material in the annular gap between the unconnected ends of the tubes machined for a very close fit, thereby permitting the relative axial motion but transmitting the lateral motion associated with bending moments due to the lateral tip forces. Another alternative is to make the tubes with a very close fit and apply a low friction coating to one or both surfaces at the distal end. However, these alternatives may create a small deadband in sensor response depending on how close a fit may be reliably obtained. The expansion thermal coefficients of the inner and outer tubes must also be matched or the required close fit may bind when heated or cooled.

It should also be understood that the same decoupling effect achieved with concentric tubes as described above may potentially be achieved with alternating axial finger-like members half (or some number) of which carry the axial cable loads while the alternating (or remaining) ones carry the bending loads. Again, these members may be rigidly connected at the proximal end while they are decoupled in the axial direction at the distal end.

Figure 5A:
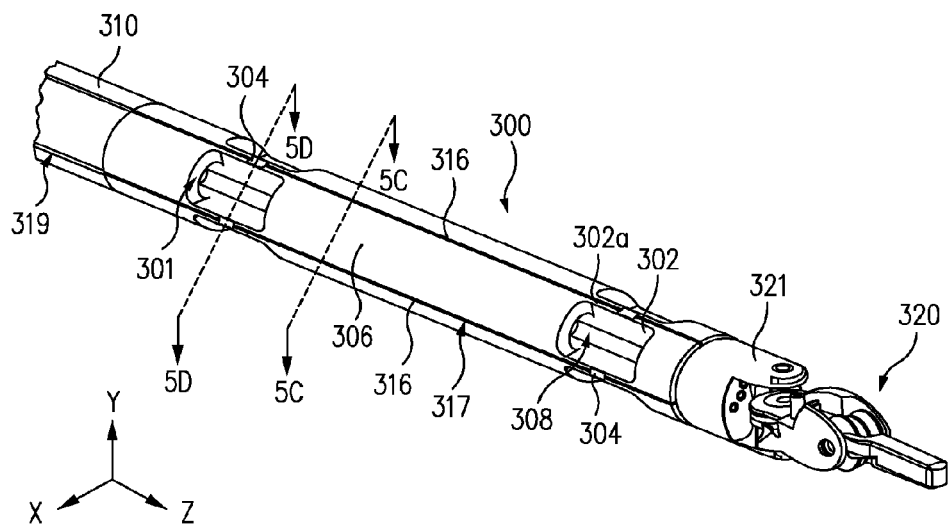
FIG. 5A is a perspective view of a force sensor apparatus in accordance with yet another embodiment of the present invention.
Figure 5B:
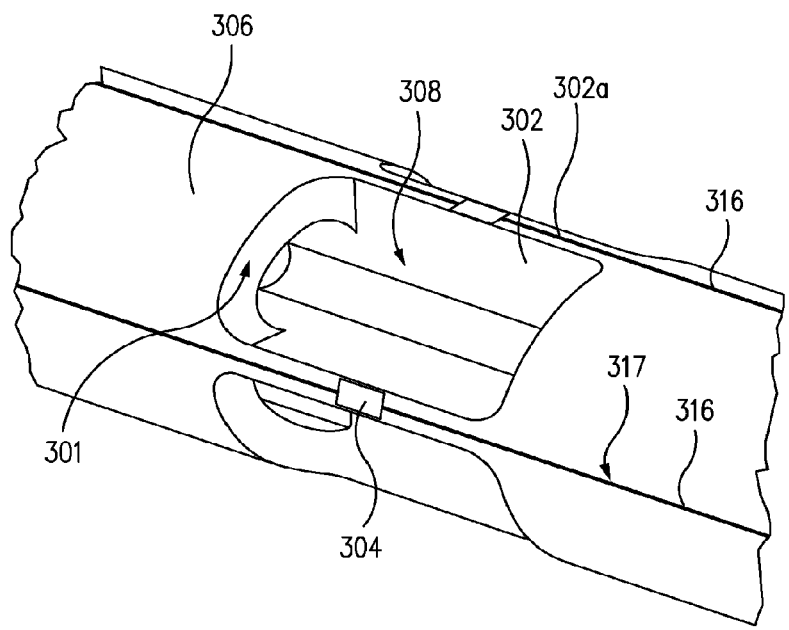
FIG. 5B illustrates an enlarged perspective view of a section of the force sensor apparatus of FIG. 5A.
Figure 5C:
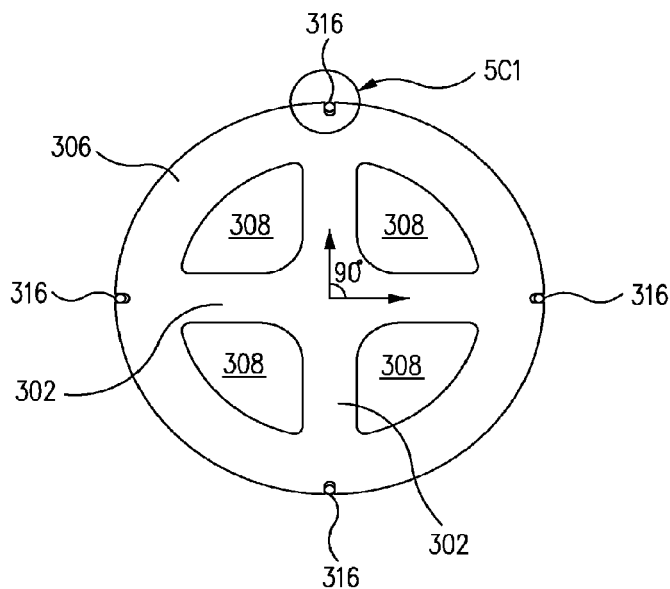
FIG. 5C illustrates a cross-sectional view of the force sensor apparatus of FIG. 5A along line 5C-5C.
Figure 5D:
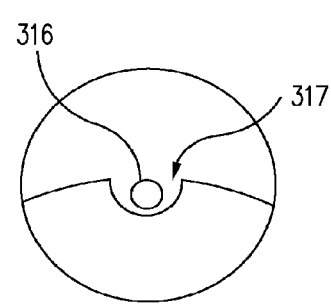
FIG. 5D illustrates a cross-sectional view of the force sensor apparatus of FIG. 5A along line 5D-5D.
Figure 5D:
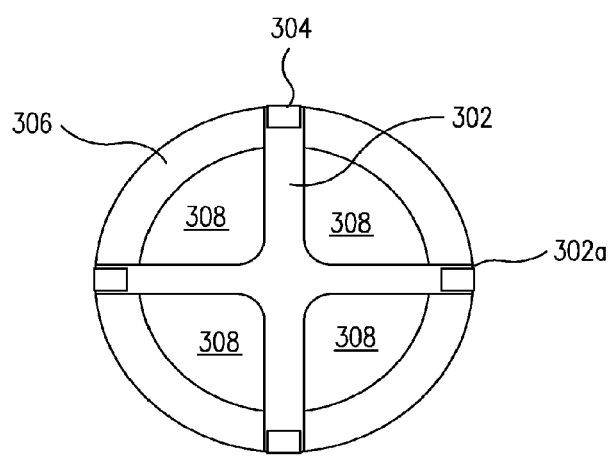
Figure 5E:
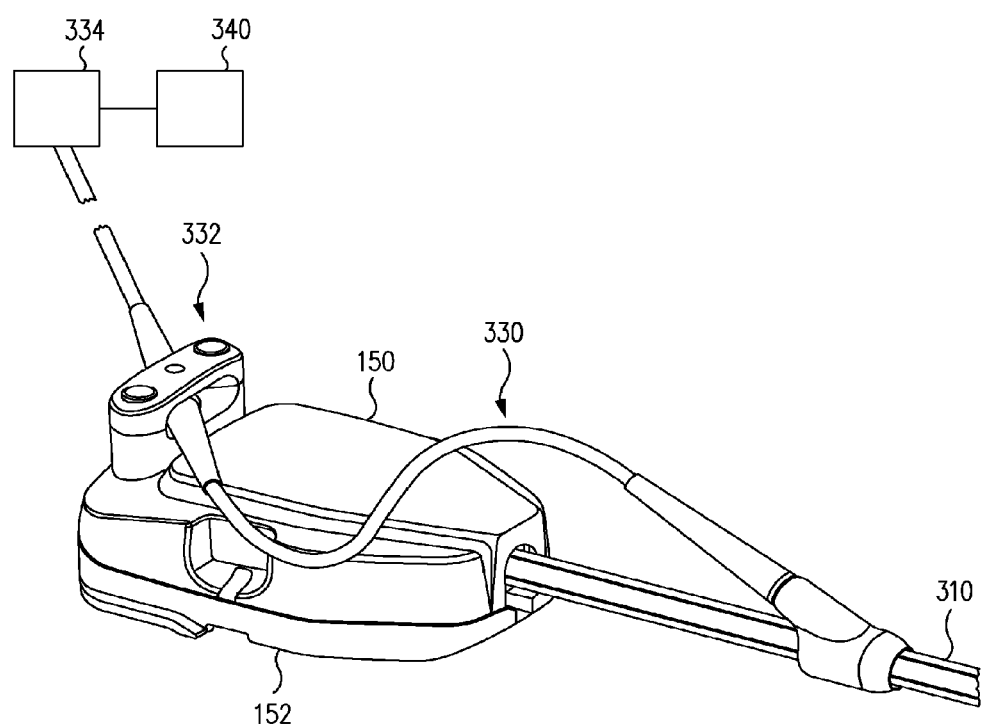
FIG. 5E illustrates a strain relief for strain gauge wires or optic fibers in accordance with an embodiment of the present invention.

Referring now to FIGS. 5A-5E, views of a surgical instrument including another force sensor apparatus 300 is illustrated in accordance with yet another embodiment of the present invention. An end portion 320, such as a surgical end effector, is coupled to force sensor apparatus 300 via a wrist joint 321. A housing 150 (FIG. 5E) is operably coupled to a proximal end of a rigid shaft 310, the housing 150 further including an interface 152 which mechanically and electrically couples the instrument to the manipulator. FIG. 5B is an enlarged perspective view of an aperture and rib section of the force sensor apparatus of FIG. 5A. FIGS. 5C and 5D are cross-sectional views of the force sensor apparatus of FIG. 5A along lines 5C-5C and 5D-5D, respectively, and FIG. 5C1 illustrates a magnified section labeled 5C1 in FIG. 5C. FIG. 5E illustrates an example proximal portion of the surgical instrument including the housing and operably coupling of the instrument to an interrogator 334 and processor 340. The descriptions of substantially similar parts or elements as those described above with respect to FIGS. 1-4 are applicable in this embodiment with respect to FIGS. 5A-5E, although redundant descriptions may be omitted.

Returning to FIG. 5A, force sensor apparatus 300 includes a generally annular tube 306 operably coupled to a distal end of rigid shaft 310 and proximal to wrist joint 321 in accordance with an embodiment of the present invention. In one embodiment, tube 306 includes a number of rectangular-shaped apertures 301 cut from tube 306 and a plurality of radial ribs 302 forming through passages 308 for passage of actuation cables, wires, tubes, rods, and/or flushing fluids. Ribs 302 run along and radiate from the z-axis centerline of tube 306, and a number (e.g., 3, 4, 6, or 8) of strain gauges 304 are oriented parallel to the lengthwise z-axis of the tube and mounted to an outer rib surface 302a. The strain gauges may be inlaid into grooves or a depressed area 317 on the outer rib surface 302a in one example.

In the embodiment illustrated in FIGS. 5A-5D, force sensor apparatus 300 includes two sets of four apertures 301 cut from the wall of tube 306 at separate axial locations along tube 306. Each of the ribs 302 are separated by 90 degrees measured about the z-axis centerline of tube 306, which forms a cruciform cross-sectional view of the ribs 302, as shown in FIGS. 5C and 5D. Ribs 302 form four through passages 308 for passage of actuation cables, wires, tubes, and/or rods. Furthermore, ribs 302 may extend along the entire length of tube 306 thereby forming internal through passages along the entire length of tube 306, or ribs 302 may extend along a portion(s) of the length of tube 306, thereby forming internal through passages along a portion or portions of the length of tube 306.

Force sensor apparatus 300 is capable of sensing bending moments applied to its distal end due to lateral forces applied to the wrist joint or its specialized end portion. Advantageously, apertures 301 and ribs 302 provide for regions of controlled stress and strain when subjected to bending moments, which may be measured by fiber optic strain gauges 304 embedded in grooves along an outer surface of the ribs and sensor body parallel to the lengthwise z-axis of tube 306. Through passages 308 permit cables, wires, tubes, or rigid tendons to pass through the sensor apparatus body to actuate the distal wrist joint(s) and/or control the end portion.

In one example, tube 306 and ribs 302 may be made of a sufficiently strong but elastic material to allow sensing of stress and strain without mechanical failure. Tube 306 and ribs 302 are further comprised of material with a sufficiently low modulus of elasticity to give a sufficient strain signal under an applied load, a sufficiently high strain at yield to give adequate safety margin above the maximum design load, and a sufficiently high thermal diffusivity to promote rapid thermal equilibrium (therefore reducing thermal disturbances to sensor output signals) when subject to localized or asymmetric thermal disturbances from tissue contact or endoscope illumination. In particular, the plurality of radial ribs 302 may be comprised of a high thermal diffusivity material, such as an aluminum alloy (e.g., 6061-T6 aluminum) or a copper alloy (e.g., GlidCop® AL-60) to reduce the temperature difference between opposing gauges under transient thermal disturbances while providing a direct thermal pathway between opposing gauges.

In one example, tube 306 may be comprised of metal alloys, treated metals, or plated metals, such as of aluminum, copper, or silver, which allow for adequate strain, mechanical failure safety margin, and high thermal diffusivity. In a further example, 6061-T6 aluminum, which is an aluminum alloy that is heat treated and aged, GlidCop® AL-60, which is copper that is dispersion strengthened with ultrafine particles of aluminum oxide, or a dispersion strengthened silver, may be used to form tube 306 and ribs 302.

Advantageously, the present invention allows for a low bending moment of inertia to increase a strain signal to noise signal ratio consistent with a materials choice and rib design meeting the need for high thermal diffusivity and a direct thermal path between opposing strain gauges while also providing passage for actuation cables, wires, tubes, and/or rods.

Wire leads or optic fibers 316 (e.g., shielded twisted pairs, coax, or fiber) coupled to the strain gauges 304 may be inlaid into grooves 317 on tube 306, the outer rib surface 302a, and matching grooves 319 in shaft 310 of the surgical instrument. The wire leads or optic fibers 316 may then be embedded in an adhesive potting compound such as epoxy.

As disclosed in U.S. patent application Ser. No. 11/537,241, filed Sep. 29, 2006, the contents of which have been previously incorporated by reference, strain gauges 304 may be spaced in a ring at intervals around the circumference of the tube 306 mounted on ribs 302 (e.g., 3 gauges at 120 degrees, 4 gauges at 90 degrees, or 4 gauges at 70 and 110 degrees). The signals from the sensors are combined arithmetically in various sums and differences to obtain measures of three perpendicular forces (e.g., $F_x$, $F_y$, and $F_z$) exerted upon the instrument tip and the torques about the two axes perpendicular to the shaft axis (i.e., axes x and y). In accordance with the present invention, the measurement of the forces is made independent of the orientation and effective lever arm length of an articulated wrist mechanism at the distal end of the instrument as well as wrist friction moments and actuator cable tensions when two axially separated sets or rings of gauges are utilized. Forces exerted against end portion 320 are detected by the force sensing elements, which may be operably coupled to the servo control or surgeon display means via an interrogator 334 or to a processor 340 for notifying the surgeon of these forces (e.g., via master(s) or a display means). It is understood that by adding a second ring of similarly oriented gauges (e.g., two sets of 3 gauges or two sets of 4 gauges) at a different position along the z-axis of the tube, additional applied torque information (e.g., $T_x$ and $T_y$) can be obtained, and dependence of the force data on instrument wrist length, orientation, and resulting jaw distance and cable tensions, can be eliminated.

In one example, various strain gauges may be used, including but not limited to conventional foil type resistance gauges, semiconductor gauges, optic fiber type gauges using Bragg grating or Fabry-Perot technology, or others, such as strain sensing surface acoustic wave (SAW) devices. Optic fiber Bragg grating (FBG) gauges may be advantageous in that two sensing elements may be located along one fiber at a known separation, thereby only requiring the provision of four fibers along the instrument shaft. Fiber optic gauges may also be desirable because of their resistance to disturbance from cautery and other electromagnetic noise.

Both fiber technologies require an interrogator unit, such as interrogator unit 334 (FIG. 5E) that decodes the optically encoded strain information into electrical signals compatible with the computer control hardware of the robotic surgical system. A processor 340 (FIG. 5E) operably coupled to the interrogator unit 334 may then be used to calculate forces according to the signals from the strain gauges/sensors.

For resistive foil or semiconductor strain gauges, active components such as bare die op-amps and passive components such as secondary resistors or capacitors may be attached adjacent to the strain gauges connected by bond wires or thick film circuit traces in the manner of hybrid circuits to amplify, filter, and/or modulate the gauge output signals to reject noise sources. Such components are not needed for fiber optic gauges.

In accordance with an embodiment of the present invention, force sensor apparatus 300 is a separately manufactured module or part adapted for incorporation as part of the shaft 310 of a laparoscopic surgical instrument at a prescribed distance from the tip where there may be an articulated wrist with specialized jaws, cutting devices, or other end portion 320. A proximal portion of tube 306 operably couples to the shaft 310 of the surgical instrument and a distal portion of tube 306 operably couples to wrist joint 321. In one example, the diameter of the completed force sensor apparatus matches the diameter of the instrument shaft, thus allowing the entire assembly of the instrument (including the coupled force sensor apparatus) to pass through a cannula or a seal without added friction or snagging. In other embodiments, the surgical instrument may be manufactured with a force sensor portion integrated as a part of shaft 310 (i.e., force sensor apparatus 300 is not separable from the shaft).

Similar to the embodiments described above, the surgical instrument to which force sensor apparatus 300 couples may also include a service loop 330 (FIG. 5E) of conductive traces or optic fibers at the proximal end of the instrument shaft 310 and a cable swivel mechanism 332 permitting the substantially free rotation of the instrument shaft while conducting the input gauge excitation power or light and electrical or optical output gauge signals to the interrogator unit 334.

Similar to the embodiments described above, the housing 150 operably interfaces with a robotic manipulator arm, in one embodiment via a sterile adaptor interface. Applicable housings, sterile adaptor interfaces, and manipulator arms are disclosed in U.S. patent application Ser. No. 11/314,040 filed on Dec. 20, 2005, and U.S. patent application Ser. No. 11/613,800 filed on Dec. 20, 2006, the full disclosures of which are incorporated by reference herein for all purposes. Examples of applicable shafts, end portions, housings, sterile adaptors, and manipulator arms are manufactured by Intuitive Surgical, Inc. of Sunnyvale, Calif.

In a preferred configuration, end portion 320 has a range of motion that includes pitch and yaw motion about the x- and y-axes and rotation about the z-axis. These motions as well as actuation of an end effector are provided via cables, wires, tubes, and/or rods running through passages 308 and into the housing that transfer motion from the manipulator arm. Embodiments of drive assemblies, arms, forearm assemblies, adaptors, and other applicable parts are described for example in U.S. Pat. Nos. 6,331,181, 6,491,701, and 6,770,081, the full disclosures of which are incorporated herein by reference for all purposes.

It is noted that various surgical instruments may be improved in accordance with the present invention, including but not limited to tools with and without end effectors, such as jaws, scissors, graspers, needle holders, micro-dissectors, staple appliers, tackers, suction irrigation tools, clip appliers, cutting blades, hooks, sealers, lasers, irrigators, catheters, and suction orifices. Alternatively, the surgical instrument may comprise an electrosurgical probe for ablating, resecting, cutting or coagulating tissue. Such surgical instruments are manufactured by Intuitive Surgical, Inc. of Sunnyvale, Calif.

For the sensing methods and apparatus mentioned above, it may be advantageous to use a calibration process in which combinations of forces and torques are applied to the instrument tip serially, simultaneously, or in combinations while correction factors and offsets are determined to apply to the theoretical equations for combining the gauge outputs to obtain $F_x$, $F_y$, $F_z$, $T_x$, and $T_y$. This calibration may be done either by directly calculating the correction factors and offsets or by a learning system such as a neural network embedded in the calibration fixture or in the instrument itself. In any calibration method, the calibration data may be programmed into an integrated circuit embedded in the instrument so that the surgical system using the individual instrument can correctly identify and apply its correction factors and offsets while the instrument is in use.

Advantageously, force sensor apparatus 300 of the present invention is adaptable to the size and shape constraints of robotic endoscopic surgical instruments and is suitable for a variety of instruments. Furthermore, force sensor apparatus 300 may be manufactured, tested, and calibrated as a separate modular component and brought together with other components in the conventional instrument assembly process or as an integrated part of the instrument shaft 310. Also, the sensor may be a slip-on module with suitable electrical contacts that mate with contacts on the instrument shaft permitting a higher value sensor to be used with lower cost instruments of limited cycle life.

The present invention is not limited to rib orientation or a certain number of ribs, sets of ribs, strain gauges, or tube apertures, and FIGS. 6A-6C1, 7A-7B1, 8, and 9A-9C illustrate force sensor apparatus in accordance with other embodiments of the present invention. The descriptions of substantially similar parts or elements as those described above with respect to FIGS. 5A-5E are applicable in these embodiments although redundant descriptions may be omitted.

Figure 6A:
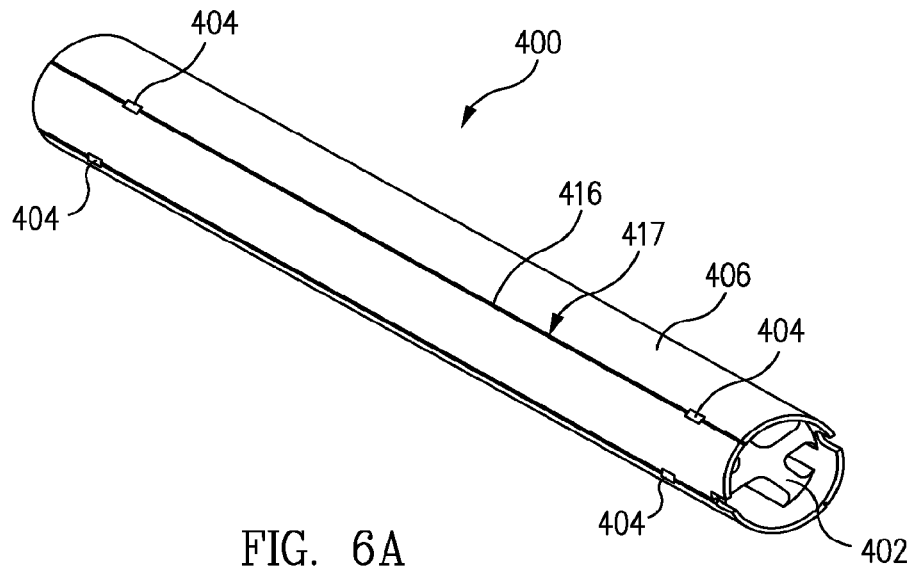
FIGS. 6A and 6B illustrate perspective views of another force sensor apparatus and an enlarged section of the force sensor apparatus in accordance with another embodiment of the present invention.
Figure 6B:
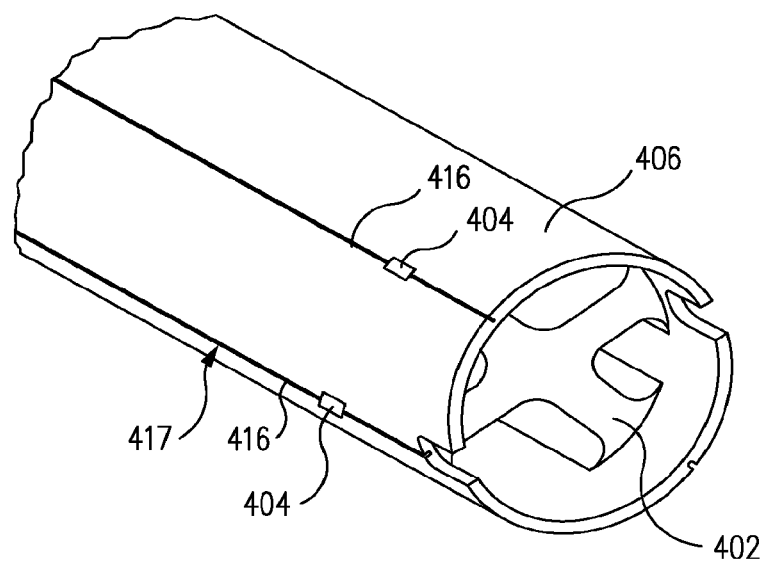

Referring now to FIGS. 6A-6C1, a force sensor apparatus 400 is illustrated, the force sensor apparatus 400 including four ribs 402 paired at skewed angles (e.g., 70 degrees and 110 degrees) about a z-axis centerline of a tube 406. Ribs 402 extend radially within tube 406 from the z-axis centerline of the tube providing four through passages 408a and 408b for passage of actuation cables, wires, tubes, and/or rods. Advantageously, a larger through passage 408a utilizing skewed angles allows for easier passage of cables, wires, tubes, and/or rods through tube 406 (e.g., three hypodermic tubes may be passed per 110 degree channel). In this embodiment, as can be seen in FIG. 6A, tube 406 does not include apertures through the wall of tube 406. However, the combined stiffness of tube 406 and ribs 402 still allow for a strong strain signal to noise signal ratio consistent with a materials choice and rib design meeting the need for high thermal diffusivity and a direct thermal path between opposing strain gauges while also providing passage for actuation cables, wires, tubes, and/or rods.

Similar to the embodiments disclosed above, a number of strain gauges 404 are oriented parallel to the lengthwise z-axis of the tube and mounted to an outer rib surface 402a. The strain gauges may be inlaid into grooves or a depressed area 417 on the outer rib surface 402a in one example. Wire leads or optic fibers 416 (e.g., shielded twisted pairs, coax, or fiber) coupled to the strain gauges 404 may be inlaid into grooves 417 on tube 406, the outer rib surface 402a, and matching grooves 417 in a shaft of the surgical instrument. The wire leads or optic fibers 416 may then be embedded in an adhesive potting compound such as epoxy.

Referring now in particular to FIGS. 6C and 6C1, an end view of force sensor apparatus 400 and a magnified section labeled 6C1 in FIG. 6C are respectively illustrated. A thermal shielding over the strain gauges may be provided in accordance with another embodiment of the present invention. In one example, a thermal shunt shell 452 is provided over tube 406 with an insulating fluid filled gap 450 being provided between the outer surface of tube 406 and the inner surface of thermal shunt shell 452. Thermal shunt shell 452 may be comprised of a high diffusivity material, such as an aluminum alloy (e.g., 6061-T6 aluminum) or a copper alloy (e.g., Glid-Cop® AL-60). Optionally, a light reflective coating 453 may be provided over thermal shunt shell 452, which may deflect light and reduce localized heating of the force sensor apparatus. An insulating coating 454 may also be provided over thermal shunt shell 452, the insulating coating 454 being comprised of a substantially transparent plastic shrink polymer in one example. Advantageously, the thermal shielding over the strain gauges as described above allows for greater heat/thermal diffusion among the sensors, being particularly advantageous for mitigating asymmetric thermal loads upon the instrument. The thermal shielding described above is applicable for various embodiments of the present invention.

Figure 7A:
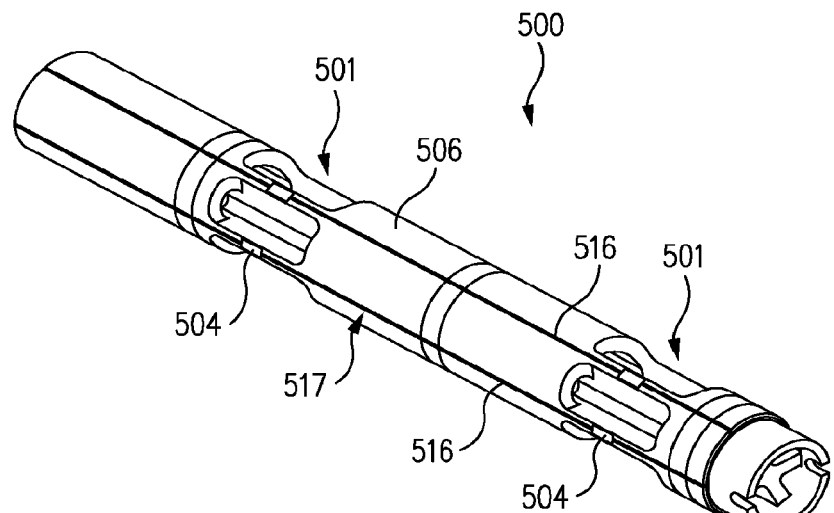
FIGS. 7A and 7B illustrate a perspective view and an end view of another force sensor apparatus including radial ribs positioned in non-uniform angles and apertures on the tube surface.
Figure 7B:
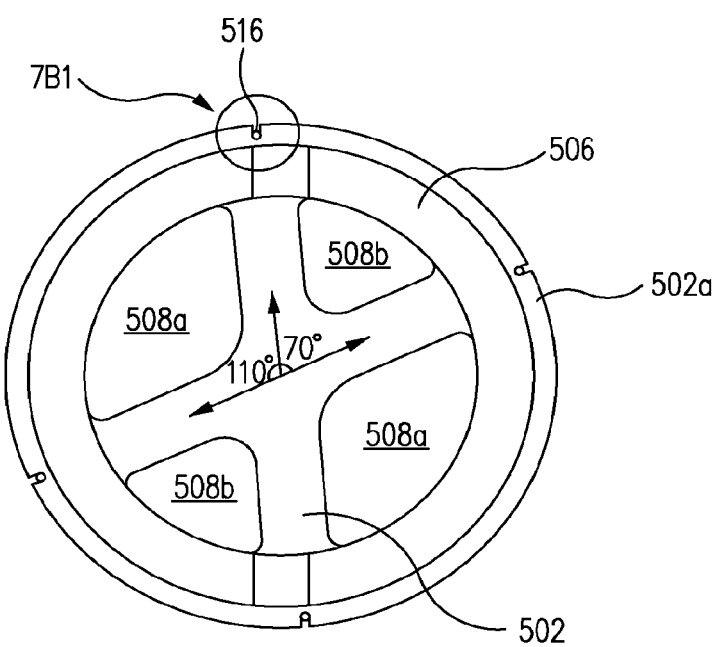

Referring now to FIGS. 7A thru 7B1, a force sensor apparatus 500 is illustrated, the force sensor apparatus 500 including four ribs 502 paired at skewed angles (e.g., 70 degrees and 110 degrees) about a z-axis centerline of a tube 506. Ribs 502 extend radially within tube 506 from the z-axis centerline of the tube providing four through passages 508a and 508b for passage of actuation cables, wires, tubes, and/or rods. Advantageously, a larger through passage 508a utilizing skewed angles allows for easier passage of cables, wires, tubes, and/or rods through tube 506 (e.g., three hypodermic tubes may be passed per 110 degree channel). In this embodiment, as can be seen in FIG. 7A, tube 506 include apertures 501 provided through the wall of tube 506. The reduced stiffness of exposed ribs 502 allow for a strong strain signal to noise signal ratio consistent with a materials choice and rib design meeting the need for high thermal diffusivity and a direct thermal path between opposing strain gauges while also providing passage for actuation cables, wires, tubes, and/or rods.

Similar to the embodiments disclosed above, a number of strain gauges 504 are oriented parallel to the lengthwise z-axis of the tube and mounted to an outer rib surface 502a. The strain gauges may be inlaid into grooves or a depressed area 517 on the outer rib surface 502a in one example. Wire leads or optic fibers 516 (e.g., shielded twisted pairs, coax, or fiber) coupled to the strain gauges 504 may be inlaid into grooves 517 on tube 506, the outer rib surface 502a, and matching grooves 517 in a shaft of the surgical instrument. The wire leads or optic fibers 516 in grooves 517 may then be embedded in an adhesive potting compound such as epoxy.

Figure 8:
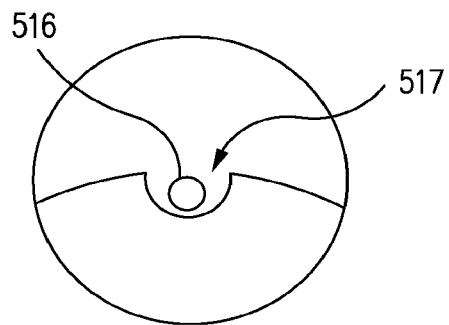
FIG. 8 illustrates an end view of another force sensor apparatus including three radial ribs in accordance with another embodiment of the present invention.
Figure 8:
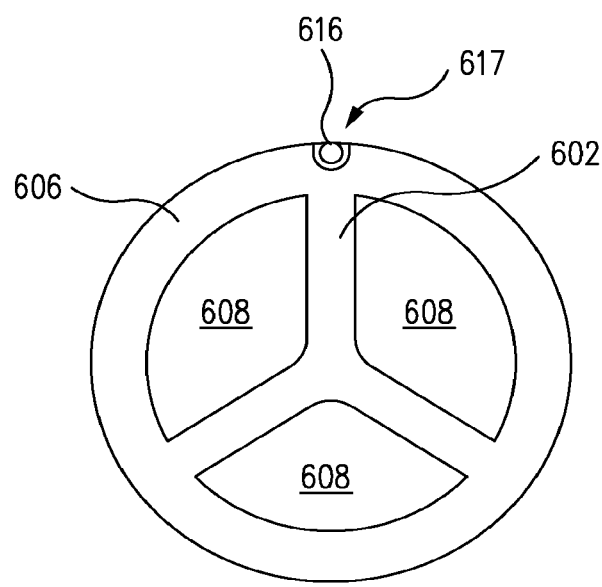

FIG. 8 illustrates a cross-sectional view of another force sensor apparatus which includes three ribs 602 separated by 120 degrees about a z-axis centerline of the force sensor apparatus tube 606. Ribs 602 provide three through passages 608. Wire leads or optic fibers 616 (e.g., shielded twisted pairs, coax, or fiber) coupled to strain gauges may be inlaid into grooves 617 on an instrument tube, an outer rib surface, and matching grooves in a shaft of the surgical instrument.

Figure 9A:
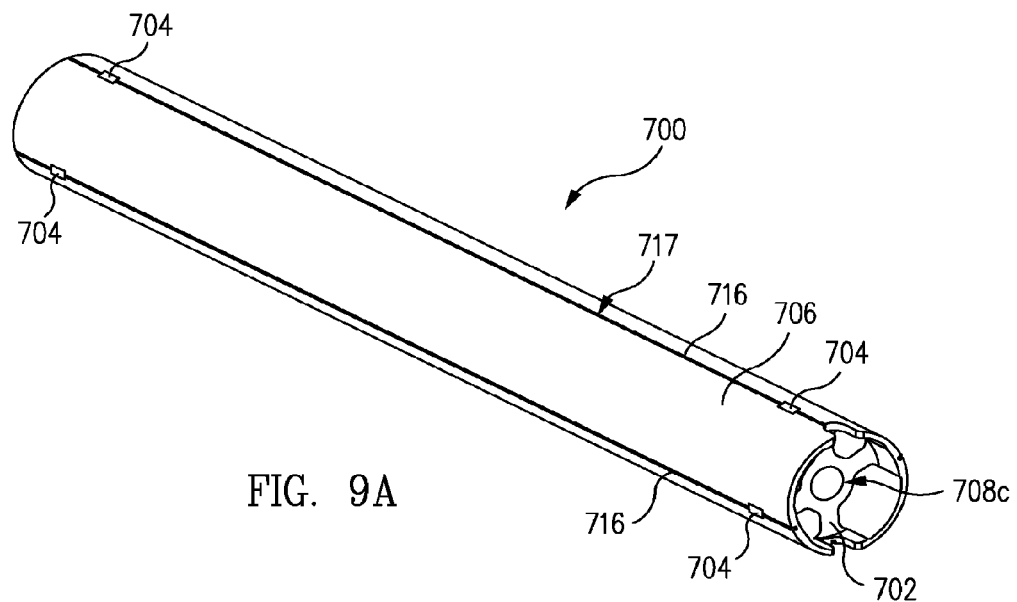
FIGS. 9A and 9B illustrate perspective views of another force sensor apparatus and an enlarged section of the force sensor apparatus, respectively, in accordance with another embodiment of the present invention.
Figure 9B:
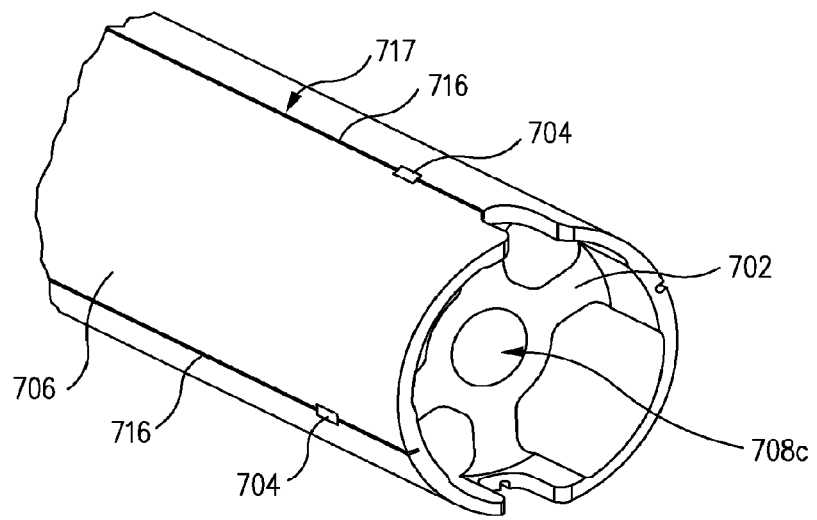
Figure 9C:
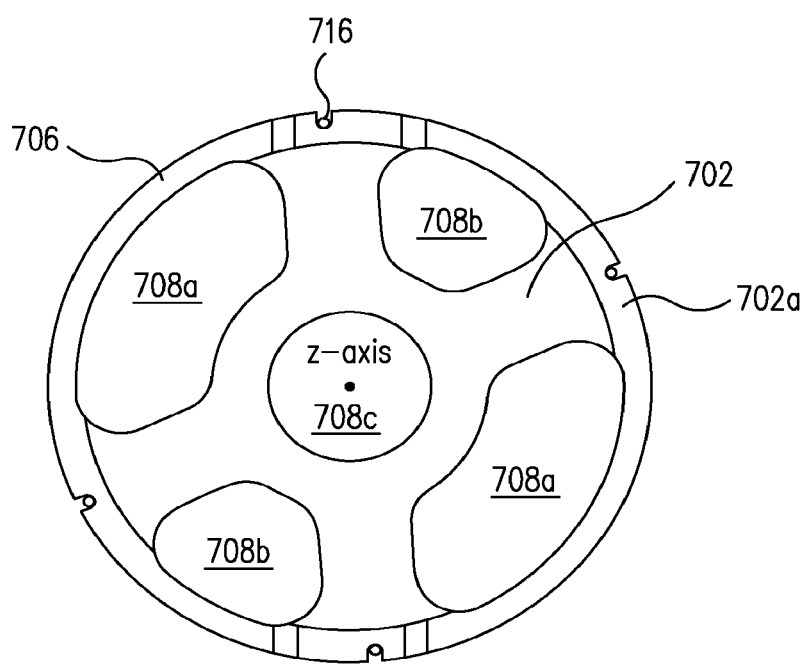
FIG. 9C illustrates an end view of the force sensor apparatus of FIGS. 9A and 9B including radial ribs positioned in non-uniform angles and a central through passage in accordance with another embodiment of the present invention.

Referring now to FIGS. 9A-9C, a force sensor apparatus 700 is illustrated, the force sensor apparatus 700 including four ribs 702 paired at skewed angles (e.g., 70 degrees and 110 degrees) about a z-axis centerline of a tube 706. Ribs 702 extend radially within tube 706 from the z-axis centerline of the tube providing through passages 708a and 708b. In this embodiment, force sensor apparatus 700 also includes a central through passage 708c along a lengthwise axis of tube 706 in accordance with another embodiment of the present invention. The through passages may be used for passage of actuation cables, wires, tubes, rods, and/or fluids. In this embodiment, as can be seen in FIG. 9A, tube 706 does not include apertures through the wall of the tube but apertures exposing portions of the interior ribs are within the scope of the present invention. Furthermore, the combined stiffness of tube 706 and ribs 702 still allow for a strong strain signal to noise signal ratio consistent with a materials choice and rib design meeting the need for high thermal diffusivity and a thermal path between opposing strain gauges while also providing passage for actuation cables, wires, tubes, rods, and/or fluids.

Similar to the embodiments disclosed above, a number of strain gauges 704 are oriented parallel to the lengthwise z-axis of the tube and mounted to an outer rib surface 702a. The strain gauges may be inlaid into grooves or a depressed area 717 on the outer rib surface 702a in one example. Wire leads or optic fibers 716 (e.g., shielded twisted pairs, coax, or fiber) coupled to the strain gauges 704 may be inlaid into grooves 717 on tube 706, the outer rib surface 702a, and matching grooves 717 in a shaft of the surgical instrument. The wire leads or optic fibers 716 may then be embedded in an adhesive potting compound such as epoxy.

Embodiments described above illustrate but do not limit the invention. It should also be understood that numerous modifications and variations are possible in accordance with the principles of the present invention. For example, the number of strain gauges and their configuration may vary but must allow for applicable force and torque determinations and noise rejection. Similarly, the number of ribs and angle between ribs may vary from those described above. Furthermore, the embodiments of force sensor apparatus described above may be integrated with a surgical instrument upon manufacture as a non-separable part of the shaft. Accordingly, the scope of the invention is defined only by the following claims.

We claim:

1. A force sensor apparatus for a surgical instrument comprising:
   a tube portion including an outer surface and a lengthwise axis;
   a plurality of radial ribs, the plurality of radial ribs being inside the tube portion, each radial rib of the plurality of radial ribs extending lengthwise in the direction of the lengthwise axis, and each radial rib of the plurality of radial ribs extending radially along a radius of the tube portion to the tube portion; and
   a plurality of strain gauges, each strain gauge of the plurality of strain gauges being at the outer surface, each strain gauge of the plurality of strain gauge being positioned and aligned lengthwise with a corresponding radial rib of the plurality of radial ribs.

2. The apparatus of claim 1, wherein the plurality of radial ribs are comprised of a high thermal diffusivity material.

3. The apparatus of claim 1, wherein the plurality of radial ribs includes one plurality selected from a group consisting of four ribs spaced apart by about 90 degrees about the lengthwise axis of the tube portion and three ribs spaced apart by about 120 degrees about the lengthwise axis of the tube portion.

4. The apparatus of claim 1, wherein the plurality of radial ribs includes two ribs spaced apart by 110 degrees about the lengthwise axis of the tube portion and two ribs spaced apart by 70 degrees about the lengthwise axis of the tube portion.

5. The apparatus of claim 1, wherein each strain gauge of the plurality of strain gauges is aligned with one other strain gauge of the plurality of strain gauges along an axis parallel to the lengthwise axis of the tube portion.

6. The apparatus of claim 1, wherein the primary strain sensing direction of each of the plurality of strain gauges is oriented parallel to the lengthwise axis of the tube portion.

7. The apparatus of claim 1, wherein the plurality of strain gauges is selected from the group consisting of a Fabry-Perot strain gauge and a fiber Bragg grating strain gauge.

8. The apparatus of claim 1, wherein the plurality of strain gauges are positioned in a plurality of grooves in the outer surface.

9. The apparatus of claim 1, further comprising at least one aperture on the outer surface of the tube portion, wherein the aperture is spaced between individual stain gauges in the plurality of strain gauges, and wherein the aperture exposes at least one of the plurality of radial ribs.

10. The apparatus of claim 1, further comprising a thermal shunt shell over the outer surface of the tube portion, and a fluid filled gap between an inner surface of the thermal shunt shell and the outer surface of the tube portion.

11. The apparatus of claim 10, further comprising an insulating material over the thermal shunt shell.

12. The apparatus of claim 10, further comprising a light reflective coating over the thermal shunt shell.

13. The apparatus of claim 1, further comprising a central through passage along a lengthwise axis of the tube portion.

14. The apparatus of claim 1, the tube portion being part of a shaft of a surgical instrument.

15. A force sensor apparatus for a surgical instrument, comprising:
   a first tube portion including an outer surface and a lengthwise axis:
   a second tube portion, the second tube portion being positioned inside the first tube portion;
   a plurality of ribs, the plurality of ribs being inside the first tube portion and outside the second tube portion, each of the plurality of ribs extending radially along a radius of the first tube portion and extending from the second tube portion to the first tube portion, and each rib of the plurality of ribs extending lengthwise in the direction of the lengthwise axis; and a plurality of strain gauges, each strain gauge in the plurality of strain gauges being at the outer surface of the first tube portion, each strain gauge in the plurality of strain gauges being positioned and aligned lengthwise with a corresponding rib of the plurality of ribs.

16. The apparatus of claim 15, wherein the plurality of ribs are comprised of a high thermal diffusivity material.

17. The force sensor apparatus of claim 15, wherein the plurality of ribs includes two ribs spaced apart by 110 degrees about the lengthwise axis of the first tube portion and two ribs spaced apart by 70 degrees about the lengthwise axis of the first tube portion.

18. The apparatus of claim 15, wherein each strain gauge of the plurality of strain gauges is aligned with one other strain gauge of the plurality of strain gauges along an axis parallel to the lengthwise axis of the first tube portion.

19. The apparatus of claim 15, further comprising a shell positioned over the outer surface of the first tube portion to form a gap between an inner surface of the shell and the outer surface of the first tube portion.

20. The apparatus of claim 15, further comprising at least one aperture on the outer surface of the first tube portion, wherein the aperture is spaced between individual stain gauges in the plurality of strain gauges, and wherein the aperture exposes at least one of the plurality of ribs.

\* \* \* \* \*